(12) United States Patent
Mula

(10) Patent No.: US 7,066,920 B1
(45) Date of Patent: Jun. 27, 2006

(54) URINE ABSORBENT POUCH FOR MALE INCONTINENCE

(76) Inventor: Anthony Mula, 4510 Ambassador Caffery, Suite E, Lafayette, LA (US) 70508

( * ) Notice: Subject to any disclaimer, the term of this patent is extended or adjusted under 35 U.S.C. 154(b) by 188 days.

(21) Appl. No.: 10/444,609

(22) Filed: May 23, 2003

Related U.S. Application Data

(63) Continuation-in-part of application No. 09/310,691, filed on May 7, 1999, now Pat. No. 6,569,135.

(51) Int. Cl.
A61F 5/44 (2006.01)

(52) U.S. Cl. .................................................... 604/349
(58) Field of Classification Search ......... 604/327–330, 604/345–349, 353
See application file for complete search history.

(56) References Cited

U.S. PATENT DOCUMENTS

| | | |
|---|---|---|
| 173,857 A | 2/1876 | Heaney |
| 807,599 A | 12/1905 | Cave |
| 2,873,740 A | 2/1959 | Wainwright |
| 3,200,451 A | 8/1965 | Breece, Jr. |
| 3,368,561 A | 2/1968 | Ericson |
| 3,406,690 A | 10/1968 | Igel |
| 3,613,123 A | 10/1971 | Langstrom |
| 3,618,606 A | 11/1971 | Brown |
| 3,858,584 A | 1/1975 | Johnson |
| 3,878,847 A | 4/1975 | Marsan |
| 4,197,849 A * | 4/1980 | Bostick ...................... 604/318 |
| 4,500,316 A | 2/1985 | Damico |
| 4,601,716 A | 7/1986 | Smith |
| 4,627,846 A | 12/1986 | Ternstrom |
| 4,644,945 A | 2/1987 | Thorner |
| 4,675,012 A | 6/1987 | Rooyakkers |
| 4,790,835 A | 12/1988 | Elias |
| 5,009,649 A | 4/1991 | Goulter |
| 5,074,853 A | 12/1991 | Bryant |
| 5,300,052 A | 4/1994 | Kubo |
| 5,478,334 A * | 12/1995 | Bernstein ..................... 604/353 |
| 5,586,978 A * | 12/1996 | Bayne ......................... 604/327 |
| 5,618,279 A | 4/1997 | Pudlo |
| 5,735,837 A | 4/1998 | Ishikawa |
| 5,810,799 A | 9/1998 | Slater |
| 5,827,257 A | 10/1998 | Fujioka |
| 5,840,073 A | 11/1998 | Olsen |
| 6,115,847 A | 9/2000 | Rosch |
| 6,129,719 A * | 10/2000 | Nozaki et al. ......... 604/385.01 |
| 6,530,909 B1 * | 3/2003 | Nozaki et al. ............. 604/349 |
| 6,569,135 B1 * | 5/2003 | Mula ......................... 604/349 |

* cited by examiner

*Primary Examiner*—Nick Lucchesi
*Assistant Examiner*—Michael M. Thompson
(74) *Attorney, Agent, or Firm*—Kean, Miller, Hawthorne, D'Armond, McCowan & Jarman, L.L.P.

(57) ABSTRACT

A urine absorbent pouch for male incontinence which completely surrounds the patient's penis, thereby minimizing the patient's exposure to wetness, is provided. The pouch is constructed from a piece of material which has a hole portion and a continuous portion, the hole portion containing a hole which is adapted to receive a patient's penis. A plurality of sealing means are located along the edges of the hole portion so when the sealing means are sealed onto the continuous portion, there is minimal contact between the sealing means and the patient. Additionally, a urine absorbent pouch for male incontinence can be created from a commercially available baby diaper by cutting a hole in the diaper and attaching additional sealing means to the portion of the diaper with the hole.

12 Claims, 6 Drawing Sheets

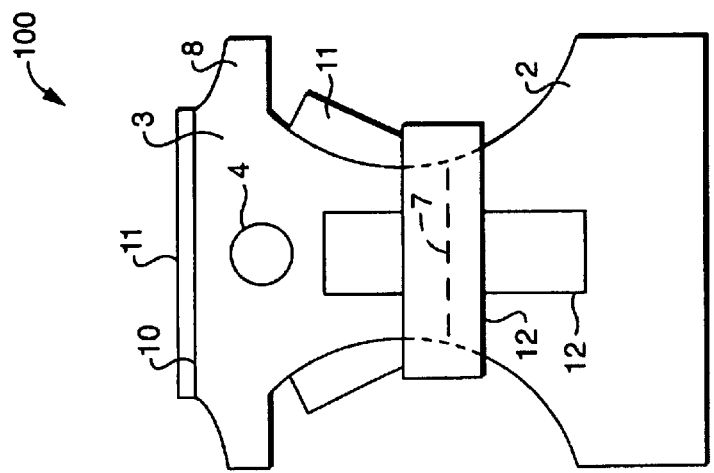
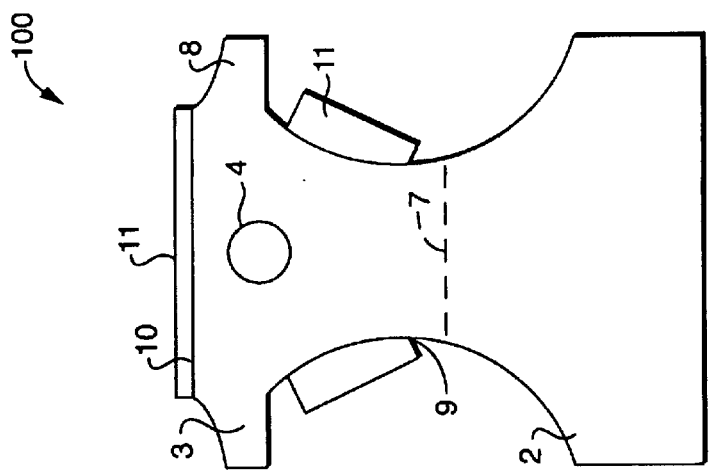
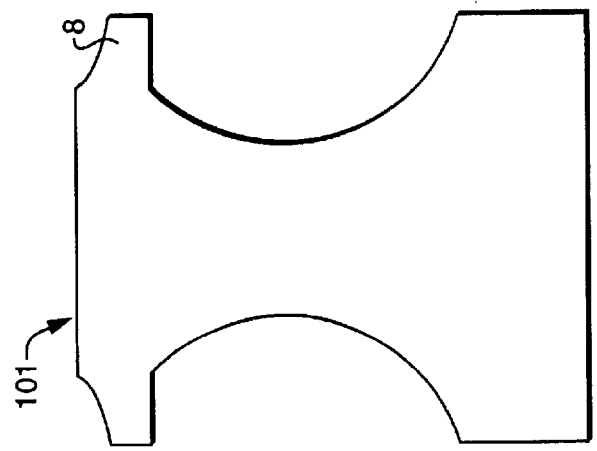

URINE ABSORBENT POUCH FOR MALE INCONTINENCE

CROSS REFERENCE TO RELATED APPLICATIONS

This is a Continuation-in-Part of U.S. application Ser. No. 09/310,691 which was filed on May 7, 1999, now U.S. Pat. No. 6,569,135 which is hereby incorporated by reference.

BACKGROUND OF THE INVENTION

1. Field of the Invention

This invention relates, generally, to incontinence products. In particular, it provides a pouch to capture urine for incontinent males.

2. Description of Related Art

Incontinence pads, diapers and other garments have been used for many years to alleviate the practical and hygienic problems encountered by people suffering from incontinence. Incontinence products generally differ from traditional baby diapers because incontinence products are designed for adults who are often incapacitated and bedridden. The adult diapers require a greater capacity of absorption, a lower propensity to cause skin irritation, an ability to withstand force of urination without being displaced, and ease of use when the patient cannot be of assistance.

Normally, these diapers have one or more inner layers of absorbent material contained in an outer layer of waterproof fabric, so that liquid voided by the patient is retained by the diaper and prevented from leaking outside the areas of contact with the patient's body. For example, U.S. Pat. No. 4,500,316 to Damico (1985) shows a diaper with a complicated support system to improve containment and avoid discharges outside the area protected by the diaper. Because of the contact between a patient's skin and wet material, skin irritation and rashes are a common problem for incontinent patients. In order to minimize this problem, garments have been developed with the specific purpose of rapidly absorbing the urine voided by the patient, thus limiting its spreading to surrounding areas. This is achieved by various means of increasing the absorption capacity of the diaper in the area immediately surrounding the patient's genitalia.

U.S. Pat. No. 3,858,584 to Johnson (1975) describes a traditional baby diaper that includes an exterior attachment for urine collection and disposal. The penis is inserted into the attachment, which is shaped like a cylindrical container, through an opening in the diaper; thus, the diaper remains dry while the urine is absorbed into the container alone. When saturated, the container can be replaced without changing the diaper. The result is that an entire new diaper need not be used unless a bowel movement has also occurred.

In U.S. Pat. No. 4,601,716 (1986), Smith describes a sanitary pouch for male use only, conceived to absorb secretions and post-urination wetness. Although intended for healthy males and not as a prosthetic for incontinence, this invention involves the idea of an absorbent and protective pocket for male adults.

In U.S. Pat. No. 4,627,846 (1986), Ternström shows a similar type of pouch, but for incontinent men. It is designed to slide under the scrotum and penis and enclose both to receive urine voided by the patient. The invention is directed to men whose incontinence is limited to urine, so that an entire diaper would not be necessary for protection.

U.S. Pat. No. 5,074,853 (1991) to Bryant describes a similar pouch for incontinent men, but is designed to wrap only around the penis. Because of its small size, it can only hold small amounts of urine voided by the patient before being changed.

Finally, U.S. Pat. No. 4,675,012 (1987) to Rooyakkers teaches a method for making yet another pouch-type absorbent diaper for incontinent males. The material is shaped to form a cup that covers the genitalia and allows air circulation to maintain skin dryness. The cup is kept in place by regular underwear against the body of the patient.

The incontinence diapers described in the prior art tend to cause skin irritation to the patient. In addition, they are cumbersome to use because of the difficulty involved in discretely and yet effectively handling a patient's genitalia during a diaper change. Some of the diapers cannot withstand the force and volume which occur during normal urination. Finally, most of the prior art devices require custom-made manufacturing since existing products can not be adapted to adult male incontinence.

What is needed is a urine absorbent pouch for male incontinence which overcomes the shortfalls of the devices which are currently known in the art.

It is an object of the present invention to provide a urine absorbent pouch for male incontinence which does not cause skin irritation to the patient.

It is another object of the present invention to provide a urine absorbent pouch for male incontinence which can withstand the force and volume of normal urination.

It is another object of the present invention to provide a urine absorbent pouch for male incontinence which be easily applied by the patient or a health care provider.

It is another object of the present invention to provide a urine absorbent pouch for male incontinence which can be easily manufactured or adapted from products already on the market.

It is another object of the present invention to provide a urine absorbent pouch for males will continue to function on a wearer who is highly mobile.

BRIEF SUMMARY OF THE INVENTION

A urine absorbent pouch for male incontinence is provided. The urine absorbent pouch includes a piece of material which has a fold line which separates a hole portion from a continuous portion. The hole portion contains a hole which is adapted to receive a patient's penis. The hole portion is defined by the fold line, two side edges adjacent to the fold line and one top edge opposite the fold line. When the material is folded along the fold line, a plurality of sealing means on the edges of the hole portion are used to create a complete enclosure around the patient's penis.

Additionally, the foregoing urine absorbent pouch for male incontinence can be made using commercially available products. A hole can be cut in a regular baby diaper such that said hole is disposed in the section of the diaper nearest the diaper's adhesive strips. A fold line is created by sealing the diaper such that the fold line separates the portion of the diaper containing the adhesive strips from the portion of the diaper adapted to receive the adhesive strips. The diaper is sealed by using the diaper's adhesive strips and sealing the diaper such that the top of the diaper portion containing the adhesive strips is folded over the diaper portion adapted to receive the adhesive strips. The patient's penis is placed through the hole before the diaper is sealed.

In one preferred embodiment the pouch is provided as an assembled pouch with a sealable flap. The pouch also includes tethers which can be used to secure the pouch to the wearer's waist and legs.

A feature of the present invention is that the urine absorbent pouch for male incontinence limits the exposure to wetness to the patient's penis only. By limiting the contact, the surrounding skin remains dry.

Another feature of the present invention is that the urine absorbent pouch for male incontinence is large enough to withstand the force and volume which occur during normal urination.

Another feature of the present invention is that the urine absorbent pouch for male incontinence be easily applied by the patient or a health care provider. The patient is not required to be lifted, as is necessary for the changing of a diaper. The urine absorbent pouch for male incontinence can be changed easily and without any cooperation by the patient, who may be unable or unwilling to act in concert with his caretaker.

Another feature of the present invention is that one embodiment of the invention can be adapted from products already on the market, such as baby diapers and sanitary napkins.

It is an advantage of the present invention that the incontinence device does not need to be changed as frequently as other male incontinence devices.

It is another advantage of the present invention that the urine absorbent pouch for male incontinence provides a cost savings as compared to traditional adult diapers.

It is another advantage of the present invention that the urine absorbent pouch for male incontinence prevents the sores and discoloration associated with urine remaining in contact with the skin for prolonged periods.

It is another advantage of the present invention that the urine absorbent pouch for male incontinence helps speed up the healing process of damaged skin by not allowing urine to remain in contact with the damaged tissue.

These and other objects, advantages, and features of this invention will be apparent from the following description.

BRIEF DESCRIPTION OF THE DRAWINGS

FIG. 5 is a plan view of a commercially available baby diaper.

FIG. 6 is a plan view of a preferred embodiment of the invention as a modification of a commercially available baby diaper.

FIG. 7 is a plan view of a preferred embodiment of the invention as a commercially available baby diaper which is modified further.

DETAILED DESCRIPTION OF THE INVENTION

Figure 1:
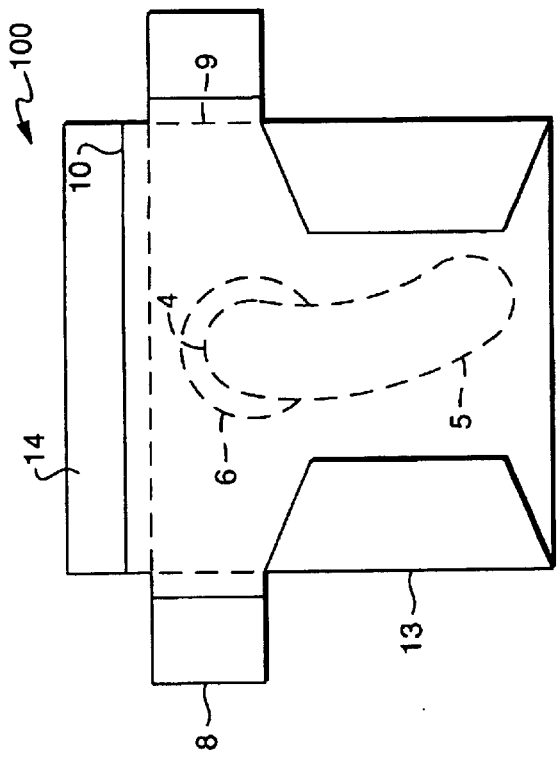
FIGS. 1 through 4 are plan views of a preferred embodiment of the invention, showing a sequence of application.

Referring to FIG. 1, a preferred embodiment of urine absorbent pouch 100 for male incontinence is shown. Pouch 100 is constructed from material 1 which normally has a substantially waterproof outer layer and an absorbent inner layer. As is known in the art, the inner layer acts to draw urine away from the patient, and the outer layer confines the urine to pouch 100. If the outer layer is thick enough and urine absorbent pouch 100 is changed often enough, it does not have to be substantially waterproof.

Material 1 is divided into continuous portion 2 and hole portion 3. Hole portion 3 contains hole 4 adapted to receive patient's penis 5 (shown in FIG. 2). The great majority of patients will be able to fit their penises 5 through the same sized hole 4. The fit does not have to be exact because as long as penis 5 is long enough to point away from hole 4, the absorbent material will keep the patient dry.

Certain applications, such as when the patient is somewhat mobile or if patient's penis 5 is very small, will require a certain degree of snugness. This can be achieved by various hole designs.

In its most basic form, the hole will merely be a slit cut in the material. More effective holes will have circular elastic band 6 surrounding hole 4. Elastic band 6 should result in sufficient tension around penis 5 to keep it from easily sliding out of hole 4, but not so tight as to create discomfort. An alternative means to create a snug fit may consist of concentric perforated circles which may be torn out depending on the size of the specific patient.

Other hole designs may include a sleeve which fits around penis 5. The sleeve would provide multiple contact points with penis 5 so that less irritation would be localized in one area. Such a sleeve could be made out of a flexible cloth, or could be held in place by an elastic ring. Although an elastic ring would localize tension in one area, the ring could be rolled up and down the sleeve on a regular basis, providing different contact points. Sleeve 5 could also be constructed of pliable material similar to that used for condoms.

For patients who are very mobile, pouch 100 must be held in place by additional means. Normal brief-style underwear is sufficient to keep pouch 100 in place. Additionally, an elastic waistband can be attached to material 1 to keep pouch 100 in place. It may be desirable for some patients to also wear adult diapers in addition to pouch 100. In such a case, outer-garments are still desirable to keep pouch 100 in place. Brief-style underwear can still be used over both pouch 100 and the adult diaper.

The positioning of hole 4 may be important. If hole 4 is in the center of hole portion 3, then, depending on the size of material 1, there may not be enough room for patient's penis 5. If hole 4 is off-center, then there is more room for penis 5.

Figure 2:
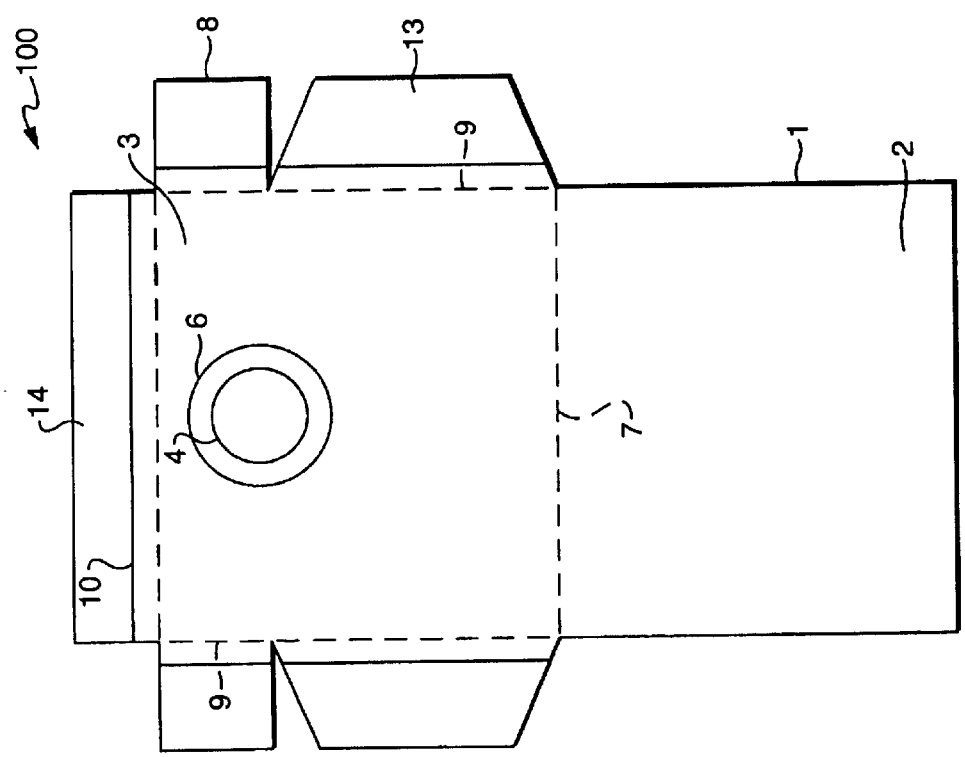

Referring to FIG. 2, material 1 must be folded along fold line 7 in order to form pouch 100. Fold line 7 must be positioned so that hole portion 3 can be sealed to continuous portion 2. Fold line 7 can be indicated by marks on material 1 or can be visualized by the caregiver by using the edges of second sealing strips 13 as a reference point.

According to one embodiment of the invention, first sealing strips 8 and second sealing strips 13 are located along each side edge 9 of hole portion 3. Side edges 9 are those side edges which are substantially perpendicular to fold line 7. The remaining edge, top edge 10, is the edge opposite fold line 7. Fold line 7, which divides hole portion 3 from continuous portion 2, is not considered an edge of either portion.

In the embodiment depicted, the sealing means used to seal continuous portion 2 to hole portion 3 are resealable adhesive strips. It will be obvious to those skilled in the art to use other types of sealing means, including but not limited to pressure-sensitive or moisture-activated strips or hook and loop fasteners (e.g. VELCRO®). It is preferable to position hole 4 away from fold line so patient may be accessed easier. The closer hole 4 is to top edge 10, the closer patient's penis will be to the opening of pouch 100.

Figure 4:
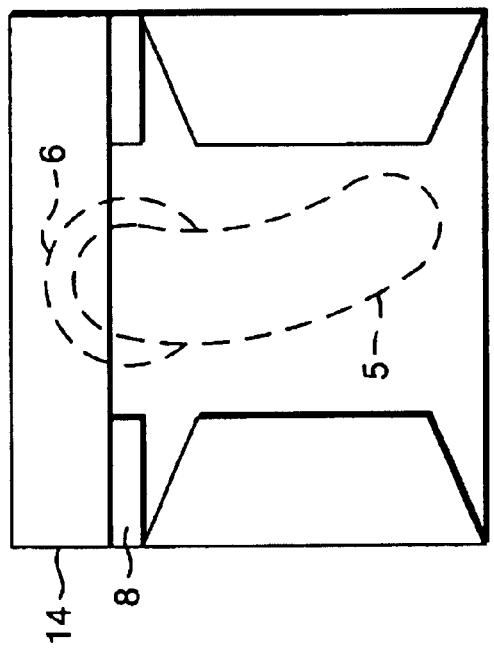
Figure 3:
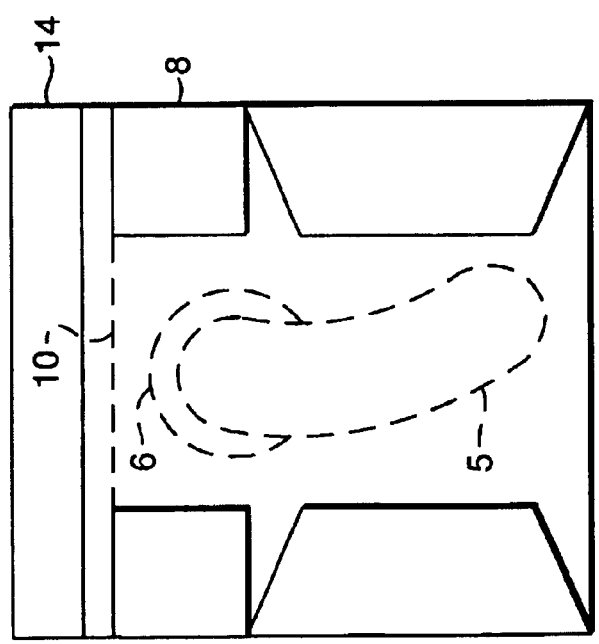

A partial enclosure can be made by sealing only second sealing strips 13. By creating only a partial enclosure, penis 5 can be properly positioned in pouch 100 prior to completely enclosing pouch 100. The manual dexterity of the person applying pouch 100 will determine whether pouch 100 must be applied before creating a partial enclosure. Very dexterous individuals will also be able to seal first sealing strips 8 prior to applying pouch 100. Referring to FIGS. 3 and 4, once the patient is properly positioned, the top sealing strip 14 can be sealed.

Sealing strips 8, 13, and 14 are attached to hole portion 3 so no rough edges touch the patient. Once sealing strips 8, 13 and 14 are sealed on continuous portion 2, sealing strips 8 do not come into contact with the patient's body, and chaffing is prevented. Sealing strips 8, 13, and 14 which are commonly used in the art include resealable adhesive strips and hook and loop fasteners (i.e., VELCRO®).

FIG. 5 shows a commercially available baby diaper 101. As will be described in the following method, diaper 101 can be easily adapted to form a urine absorbent pouch for male incontinence 100, as shown in FIG. 6. Diaper 101 is easily adaptable because it already has the desired composition of a waterproof exterior and an absorbent interior, typical diaper 101 already has one set of first sealing strips 8, and the size of a baby diaper is correct for the penis of most adult male patients.

As previously discussed, it is essential that the sealing strips 8 be on hole portion 3 and not continuous portion 2. The portion of diaper 101 which contains sealing strips 8 must, therefore, become hole portion 3. Accordingly, hole 4 is cut in the portion of diaper 101 containing sealing strips 8.

Fold line 7 divides continuous portion 2 from hole portion 3. Fold line 7 is positioned such that the edges of hole portion 3 can be sealed to continuous portion 2 with a sealing means. The sealing means can be piece of tape 11 that is attached to top edge 10 of hole portion 3 and folded onto continuous portion 2. Depending on the dexterity of the person applying pouch 100, tape 11 on top edge 10 can be sealed after patient's penis 5 is positioned through hole 4.

Preferably, the side edge 9 of hole portion 3 will also be sealed to continuous portion 2. The shape of the particular baby diaper 101 which is used may dictate whether such additional sealing means are necessary. If necessary, tape 11 can be used as the additional sealing means, being positioned below sealing strips 8, and above fold line 7.

Urine absorbent pouch for male incontinence 100 can be further improved by increasing the absorbency of the device. This can be done with additional absorbent material placed in diaper 101. As shown in FIG. 7, a convenient, commercially available product is female sanitary napkin 12. Without the addition of extra absorbent material, the modified diaper can hold about three hours of urine and the patient remain dry. With the addition of sanitary napkin 12, pouch 100 can hold from ten to twelve hours of urine and the patient remain dry.

Sanitary napkin 12 is preferably positioned such that it surrounds patient's penis 5. This can be most easily accomplished by folding sanitary napkin 12 in half and positioning the napkin so that its fold coincides with pouch's fold line 7 and lays flat against pouch 100. Alternatively, sanitary napkin 12 can be positioned so that it does not lay flat against pouch 100, but creates a channel the width of sanitary napkin 12. This is accomplished by rotating sanitary napkin 12 approximately ninety degrees from the position previously described. The creation of a channel may have the effect of causing less contact between patient's penis 5 and pouch 100.

In either position, sanitary napkin 12 can be manipulated so that it does not need to be folded in half. Although alternative methods for fitting sanitary napkin 12 inside pouch 100 include bending and making multiple folds, the positioning will be the same, i.e. either roughly parallel or perpendicular to fold line 7.

As shown in FIG. 7, additional protection can be obtained by using multiple sanitary napkins 12. By placing two sanitary napkins at roughly right angles to each other, pouch 100 can give protection for up to twelve hours. Such protection is a vast improvement over the prior art and avoids disturbing the patient overnight.

Figure 8:
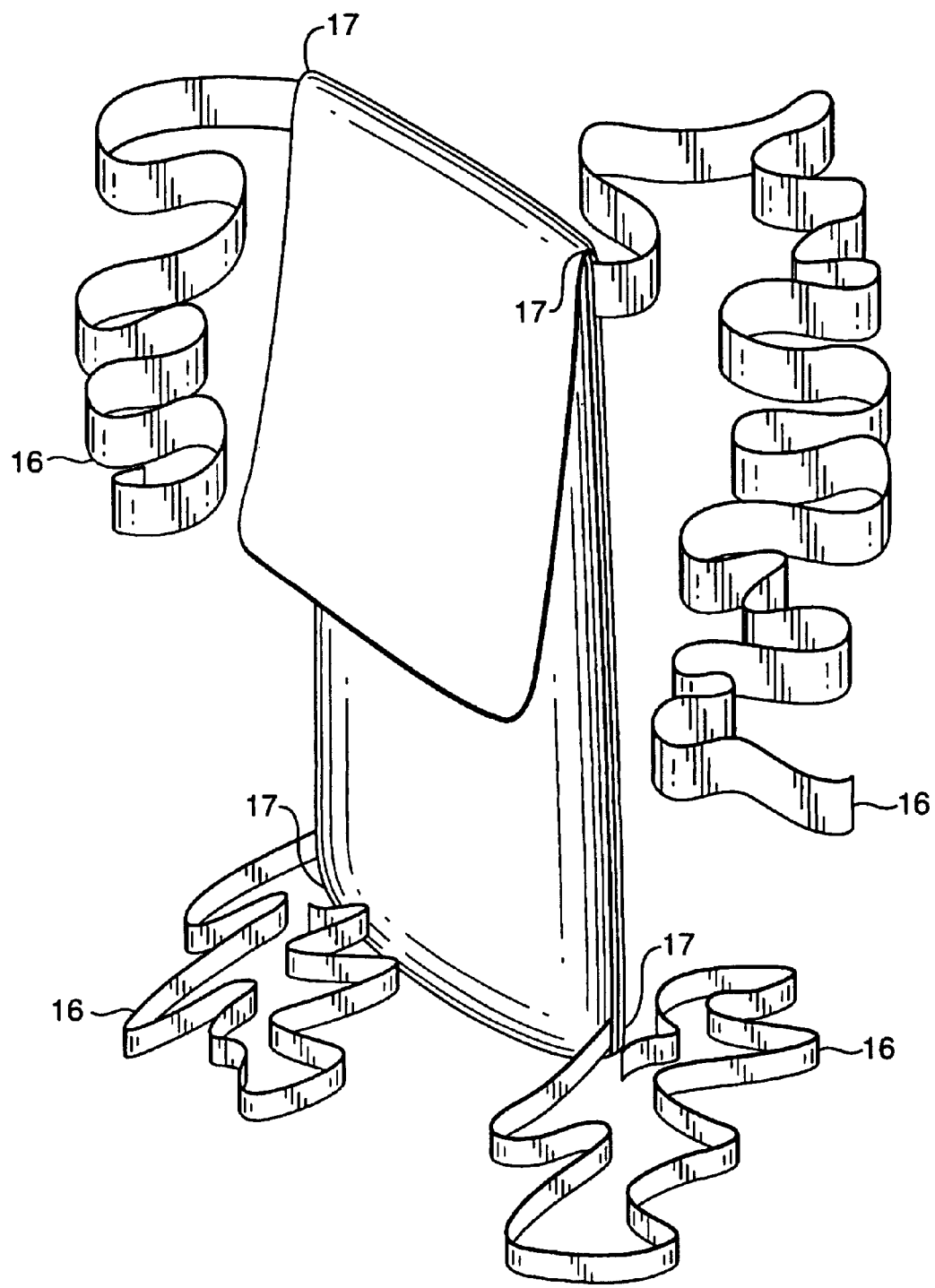
FIG. 8 is a plan view of a preferred embodiment of the invention which includes tethers.

FIGS. 8–10 depict another preferred embodiment of the invention. Tethered pouch 15 includes a plurality of tethers 16, preferably six, which are attached at the corner points 17 of tethered pouch 15.

Figure 9C:
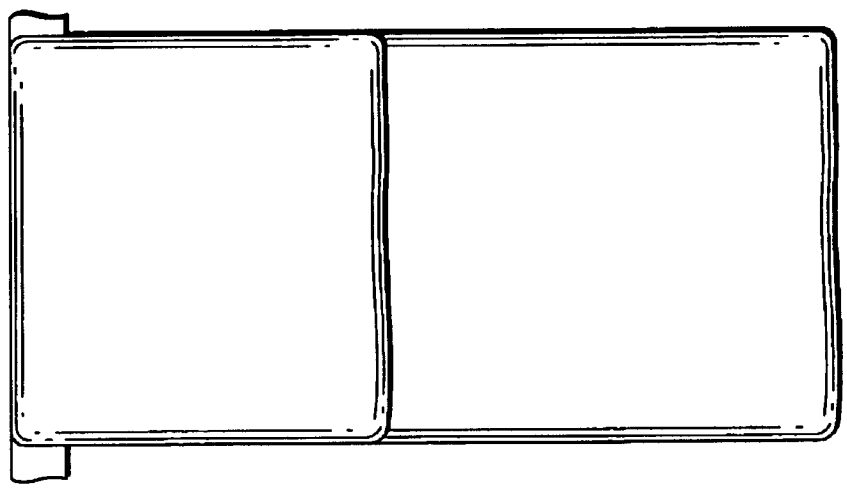
FIGS. 9A–9C are plan views which depict the various sizes of the tethered embodiment of the invention.
Figure 9B:
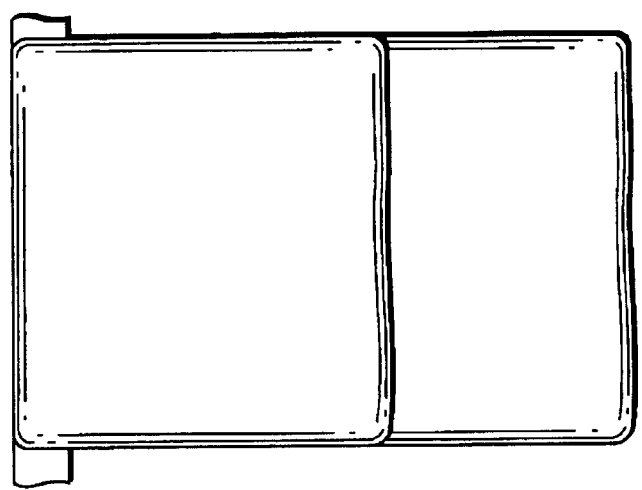
Figure 9A:
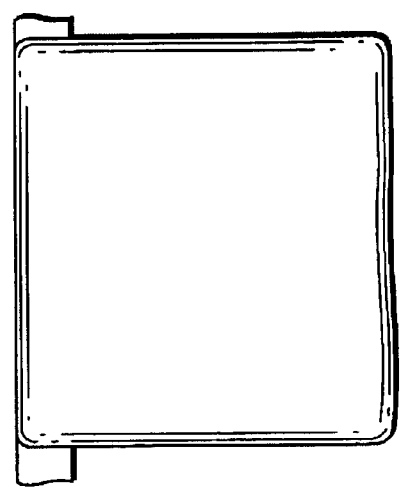

Tethered pouch 15 is constructed from material 1 which normally has a substantially waterproof outer layer and an absorbent inner layer. As is known in the art, the inner layer acts to draw urine away from the patient, and the outer layer confines the urine to tethered pouch 15. As shown in FIGS. 9A–9C, tethered pouch 15 can be constructed in multiple sizes to accommodate a variety of patients and scenarios. For example, the pouch depicted in FIG. 9A could be used with small children. The pouch in FIG. 9B could be used with incontinent adolescents and small adults. The pouch depicted in FIG. 9C could be used with large male patients, or for situations which required greater capacity for the absorption of urine.

Figures 10A, 10B:
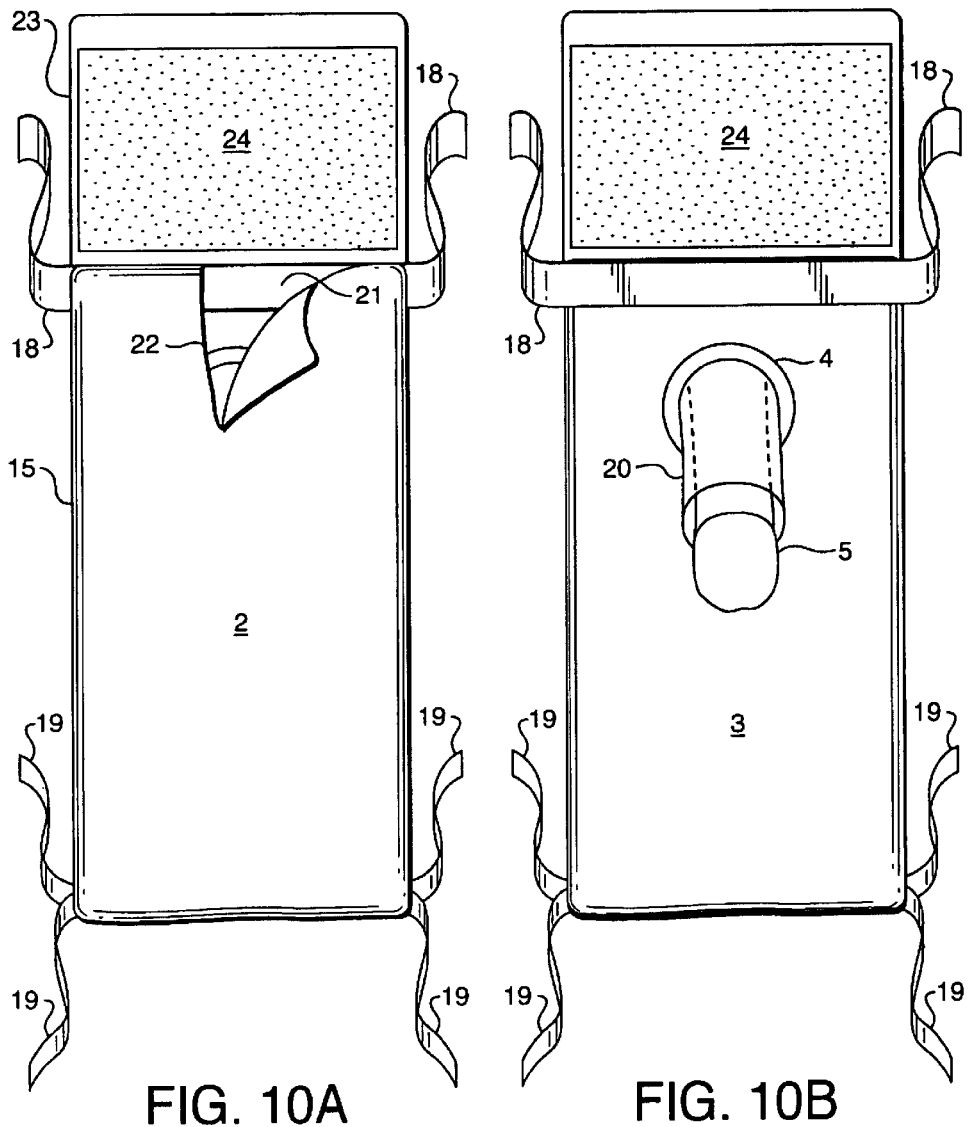
FIGS. 10A and 10B are plan views of another preferred embodiment of the invention which includes an additional slit feature.

Tethered pouch 15 will now be further described with reference to FIGS. 8–10. Material 1 of tethered pouch 15 is divided into slit portion 2 and hole portion 3. Hole portion 3 contains hole 4 adapted to receive patient's penis 5 (shown in FIG. 10B). FIG. 10A depicts tethered pouch 15 with flap 23 in the unsealed position. FIG. 10B depicts a view of hole portion 3 from what would be the inside of tethered pouch 15 with slit portion 2 removed.

Tethered pouch is especially useful when a patient is very mobile. Such mobility can be involuntary, as with bedridden or wheelchair patients who might have nerved or muscle disorders, or voluntary as with active adults or children who have no or incomplete bladder control. Tethers 16 can be used to tie tethered pouch 15 securely to the patient's body. Upper tethers 18 can be used to secure tethered pouch 15 around the wearer's waist. Lower tethers 19, two at each of the lower corner points 17, can be tied around the wearer's legs to further secure tethered pouch 15.

In a particularly preferred embodiment, hole 4 of tethered pouch 15 will be a condom-like sleeve 20. Sleeve 20 will be open at one end to allow the wearer's penis 5 to deposit urine into tethered pouch 15. The other end will be attached in a sealed manner to hole portion 3 so as to prevent urine leakage.

FIG. 8 depicts a total of six tethers 16. There are four lower tethers 19, two at each lower corner point 17, and two upper tethers 18. Those skilled in the art may wish to vary the positioning and number of tethers 16, and it is intended that the instant invention will encompass these varying placements.

Tethered pouch 16 is completely sealed except for top opening 21. Top opening 21 allows the health care provider to handle the patient's penis 5 and fully insert it into hole 4

(and sleeve 20 if present). In a particularly preferred embodiment, this access is enhanced by slit 22 in slit portion 2. Slit 22 can extend from the edge of slit portion 2 at top opening 21 to a point no lower than the point reached by flap 23 when flap 23 is in the closed position.

After the patient's penis 5 has been inserted into hole 3, the health care provider then closes flap 23 so as to cover slit 22 and top opening 21. In a particularly preferred embodiment flap 23 will include adhesive on flap underside 24. Flap underside 24 can be manufactured using a removable cover which, when removed, will expose the adhesive on flap underside 24. When flap 23 is sealed in the closed position, it will completely cover top opening 21 and slit 22.

In the embodiments depicted in FIGS. 8–10, tethers 16 are pliable tie strips, similar in their dimensions to shoe laces. It will be obvious to those skilled in the art to use a variety of materials and configurations for tethers 16. For example, tethers 16 can be made of plastic material similar to the plastic ties used on disposable garbage bags. Alternatively, tethers 16 can employ resealable adhesive strips or hook and loop fasteners (i.e., VELCRO®).

In a particularly preferred embodiment, pouch 100 or tethered pouch 15 can include absorbent crystals which can be integrated into material 1. Such crystals (not shown) or material 1 itself can also be adapted to change color when in the presence of urine. If the waterproof side of material 1 is transparent enough, this color signal feature would alert the healthcare provider that the pouch needs to be changed.

Those skilled in the art may also wish to vary the thickness or absorption of material 1 used in pouch 100 or tethered pouch 15. For example, one may wish to use more absorbent material in the part of the pouch opposite top opening 21.

There are of course other alternate embodiments which are obvious from the foregoing descriptions of the invention, which are intended to be included within the scope of the invention, as defined by the following claims.

We claim:

1. A urine absorbent pouch for male incontinence of a male patient having a penis, said pouch comprising:
   (A) a slit portion;
   (B) a hole portion having a hole therein and connected to said slit portion;
   (C) a top opening formed by said slit portion and said hole portion;
   (D) a flap contiguous with said hole portion, said flap having a flap underside; and
   (E) sealing means on said flap underside, said sealing means being adapted to close said top opening, thereby creating a substantially sealed pouch; wherein said slit portion includes a slit extending down from said top opening, and said flap is adapted to cover said slit when said pouch is closed and sealed onto said slit portion.

2. The pouch of claim 1 wherein said top opening is large enough to accommodate a person's hand being inserted so as to manipulate said patient's penis through said hole into said pouch.

3. The pouch of claim 2 said pouch has corner points, and said pouch further comprises at least one tether attached to at least one corner point.

4. The pouch of claim 1 further comprising a sleeve attached at one end to said hole.

5. A method for providing a urine absorbent pouch for an incontinent male patient, said method comprising the following steps:
   (A) providing a conventional baby diaper having adhesive strips;
   (B) cutting a hole in said diaper such that said hole is located in the diaper portion nearest said diaper's adhesive strips;
   (C) sealing the diaper in such a way as to create a fold line between the portion of the diaper containing said adhesive strips and the portion of the diaper adapted to receive said adhesive strips;
   (D) after cutting a hole in said diaper, placing the patient's penis through said hole;
   (E) sealing the diaper's adhesive strips; and
   (F) after placing said patient's penis through said hole, sealing said diaper such that the top of the diaper portion containing the adhesive strips is folded over the diaper portion adapted to receive the adhesive strips.

6. The method of claim 5 wherein said method comprises the additional step of sealing the portion of said diaper below said sealing strips and above said fold line to said portion of the diaper adapted to receive said adhesive strips.

7. The method of claim 6 wherein said method comprises the additional step of putting additional absorbent material in the diaper.

8. The method of claim 7 wherein the additional absorbent material is a sanitary napkin.

9. The method of claim 7 wherein the additional absorbent material is a plurality of sanitary napkins.

10. The method of claim 9 wherein each sanitary napkin is at roughly a right angle to the sanitary napkin directly underneath it.

11. The method of claim 6 further comprising the step of placing an outer garment over said urine absorbent pouch, said outer garment being adapted to hold the position of said urine absorbent pouch.

12. The method of claim 11 wherein said outer garment is brief-style underwear.

* * * * *